US010537738B2

(12) United States Patent
Claude et al.

(10) Patent No.: US 10,537,738 B2
(45) Date of Patent: Jan. 21, 2020

(54) ADAPTIVE TRIGGER FOR A MICROCURRENT STIMULATION DEVICE

(71) Applicant: TIVIC HEALTH SYSTEMS INC., Menlo Park, CA (US)

(72) Inventors: John Claude, Redwood City, CA (US); Christopher A. Wiklof, Everett, WA (US)

(73) Assignee: TIVIC HEALTH SYSTEMS INC., Menlo Park, CA (US)

(*) Notice: Subject to any disclaimer, the term of this patent is extended or adjusted under 35 U.S.C. 154(b) by 0 days.

(21) Appl. No.: 16/280,422

(22) Filed: Feb. 20, 2019

(65) Prior Publication Data

US 2019/0217093 A1   Jul. 18, 2019

Related U.S. Application Data

(63) Continuation of application No. PCT/US2018/029032, filed on Apr. 24, 2018.

(60) Provisional application No. 62/491,793, filed on Apr. 28, 2017, provisional application No. 62/559,792, filed on Sep. 18, 2017, provisional application No. 62/560,120, filed on Sep. 18, 2017.

(51) Int. Cl.
*A61N 1/36* (2006.01)
*A61B 5/053* (2006.01)
(Continued)

(52) U.S. Cl.
CPC .......... *A61N 1/36031* (2017.08); *A61B 5/053* (2013.01); *A61N 1/02* (2013.01); *A61N 1/04* (2013.01); *A61N 1/0428* (2013.01); *A61N 1/0456* (2013.01); *A61N 1/0472* (2013.01); *A61N 1/205* (2013.01); *A61N 1/36* (2013.01); *A61N 1/3601* (2013.01); *A61N 1/36014* (2013.01); *A61N 1/36021* (2013.01); *A61B 5/6814* (2013.01); *A61B 5/7225* (2013.01); (Continued)

(58) Field of Classification Search
CPC .............. A61N 1/3787; A61N 1/36014; A61N 1/0546; A61N 1/3925; A61N 1/36146; A61N 1/0472; A61N 1/08; A61N 1/0526; A61B 5/4836; A61B 5/0028; A61B 5/04; A61B 5/0404; A61B 5/0482; A61B 5/0484; A61B 5/486; A61B 5/6801; A61B 5/6803; A61B 5/6867; H04B 13/005
See application file for complete search history.

(56) References Cited

U.S. PATENT DOCUMENTS 4,926,880 A   5/1990  Claude et al.
5,772,605 A   6/1998  Weijand
(Continued)

FOREIGN PATENT DOCUMENTS

JP   2006-000567   1/2006
KR   20-0389849   7/2005
(Continued)

OTHER PUBLICATIONS

PCT International Search Report and Written Opinion dated Aug. 3, 2018, for PCT International Patent Application No. PCT/US2018/029032 filed Apr. 24, 2018, 21 pages.

*Primary Examiner* — Deborah L Malamud
(74) *Attorney, Agent, or Firm* — Christopher A. Wiklof; David C. Conlee; Launchpad IP, Inc.

(57) ABSTRACT

A microcurrent treatment device includes an adaptive trigger circuit configured to dynamically determine a triggering threshold for applying a therapeutic microcurrent via a treatment electrode to a nerve node on a person's face for treatment of a sinus condition.

8 Claims, 11 Drawing Sheets

(51) Int. Cl.
    *A61N 1/04*     (2006.01)
    *A61N 1/02*     (2006.01)
    *A61N 1/20*     (2006.01)
    *A61B 5/00*     (2006.01)
    *A61B 18/14*     (2006.01)
    *A61N 1/32*     (2006.01)

(52) U.S. Cl.
    CPC ............ *A61B 18/14* (2013.01); *A61N 1/326* (2013.01); *A61N 1/3603* (2017.08)

(56) References Cited

U.S. PATENT DOCUMENTS

| | | |
|---|---|---|
| 6,109,268 A | 8/2000 | Thapliyal et al. |
| 8,630,714 B1 | 1/2014 | Webb |
| 8,996,137 B2 | 3/2015 | Ackermann et al. |
| 9,002,479 B1 | 4/2015 | Unarce, Jr. |
| 9,630,003 B2 | 4/2017 | Thompson et al. |
| 10,155,108 B2 | 12/2018 | Ackermann et al. |
| 10,252,048 B2 | 4/2019 | Loudin et al. |
| 2004/0044390 A1 | 3/2004 | Szeles |
| 2007/0293918 A1 | 12/2007 | Thompson et al. |
| 2009/0030476 A1 | 1/2009 | Hargrove |
| 2011/0276107 A1 | 11/2011 | Simon et al. |
| 2013/0085551 A1 | 4/2013 | Bachinski et al. |
| 2014/0296934 A1 | 10/2014 | Gozani et al. |

FOREIGN PATENT DOCUMENTS

| | | |
|---|---|---|
| KR | 20-0414456 | 4/2006 |
| KR | 10-1534525 | 7/2015 |
| KR | 10-20150110935 | 10/2015 |

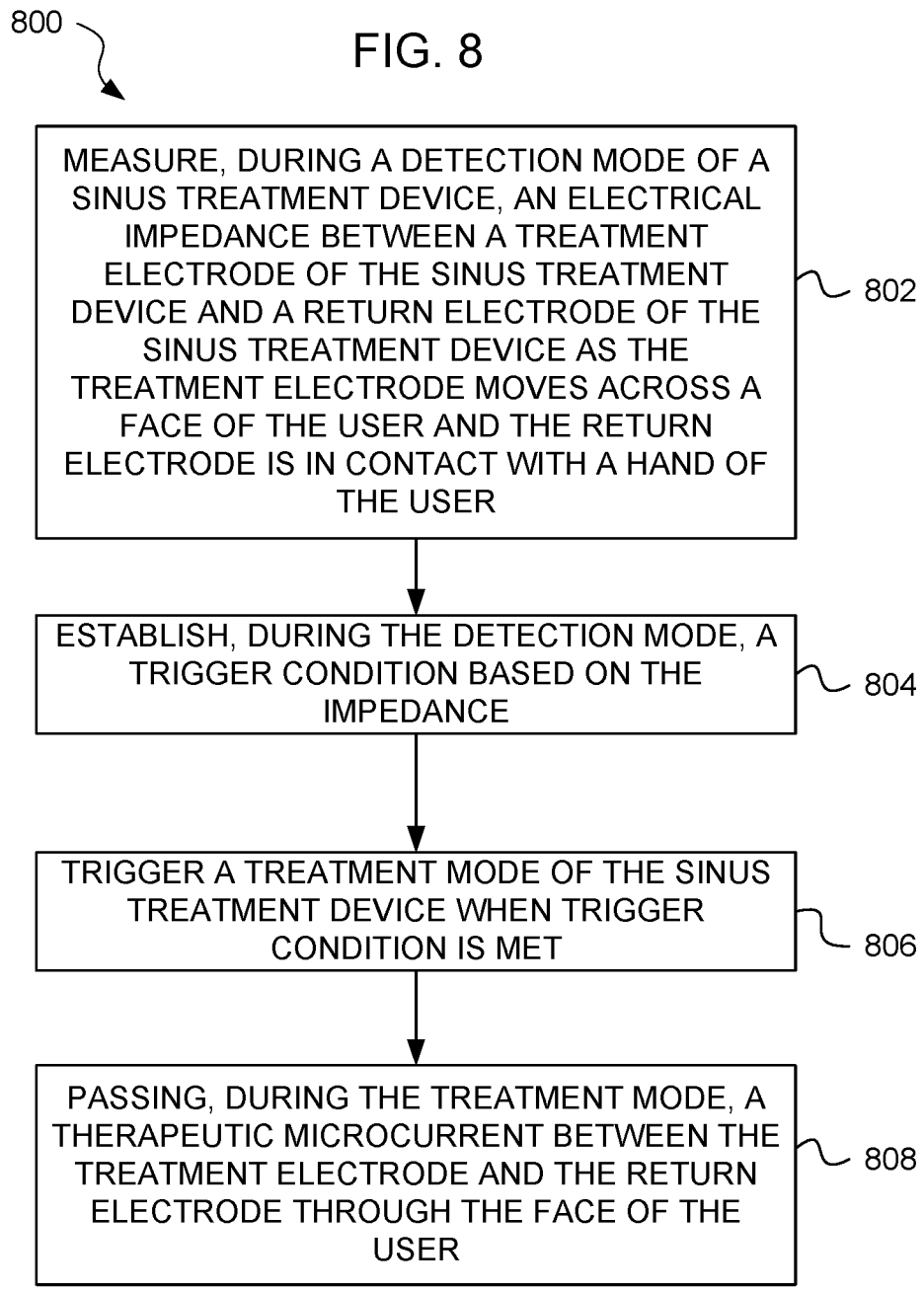

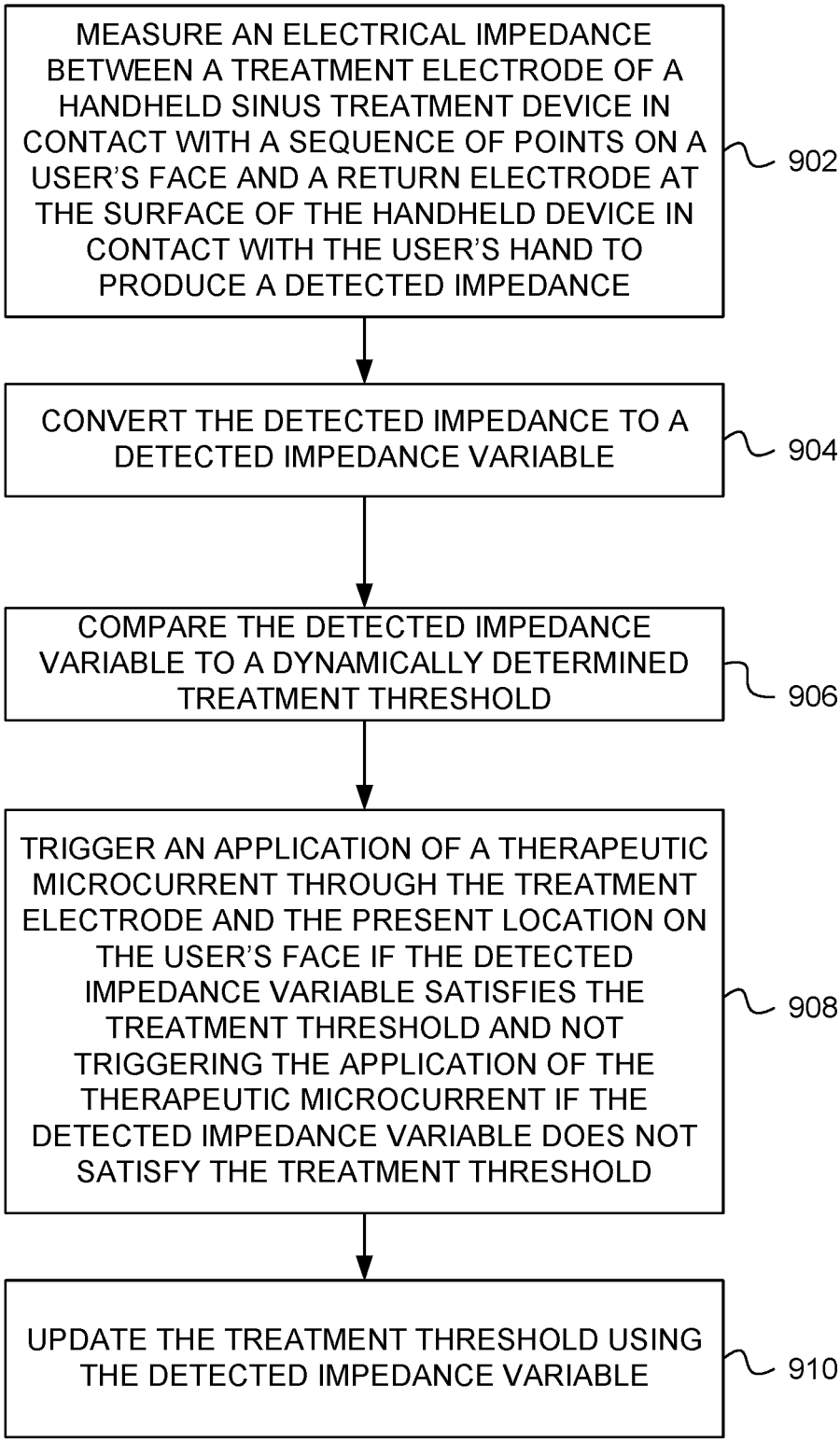

ADAPTIVE TRIGGER FOR A MICROCURRENT STIMULATION DEVICE

CROSS REFERENCE TO RELATED APPLICATIONS

The present application is a Continuation Application of co-pending International PCT Patent Application No. PCT/US2018/029032, entitled "ADAPTIVE TRIGGER FOR A MICROCURRENT STIMULATION DEVICE," filed Apr. 24, 2018. International PCT Patent Application No. PCT/US2018/029032 claims priority benefit from U.S. Provisional Patent Application No. 62/491,793, entitled "SINUS DEVICE WITH ADAPTIVE CIRCUIT," filed Apr. 28, 2017. PCT Patent Application No. PCT/US2018/029032 also claims priority benefit from U.S. Provisional Patent Application No. 62/559,792, entitled "TREATMENT DEVICE INCLUDING WIRELESS INTERFACE AND USER APPLICATION," filed Sep. 18, 2017. PCT Patent Application No. PCT/US2018/029032 also claims priority benefit from U.S. Provisional Patent Application No. 62/560,120, entitled "ADAPTIVE TRIGGER FOR A MICROCURRENT STIMULATION DEVICE," filed Sep. 18, 2017. Each of these applications, to the extent not inconsistent with the disclosure herein, is incorporated by reference.

SUMMARY

According to an embodiment, a method includes measuring, during a detection mode of a sinus treatment device, an electrical impedance between a treatment electrode of the sinus treatment device and a return electrode of the sinus treatment device as the treatment electrode moves across a face of the user and the return electrode is in contact with a hand of the user. The method includes establishing, during the detection mode, a trigger condition based on the impedance. The method includes triggering a treatment mode of the sinus therapy device when the trigger condition is met, and passing, during the treatment mode, a therapeutic microcurrent between the treatment electrode and the return electrode through the face of the user.

According to an embodiment, a handheld sinus treatment device includes a housing configured to be held in a hand of user, a treatment electrode coupled to the housing, and a return electrode positioned on the housing such that when a user holds the housing, a hand of the user is in contact with the return electrode. The handheld sinus treatment device includes a current output circuit configured to pass a treatment microcurrent between the treatment electrode and the return electrode during a treatment mode. The handheld sinus treatment device includes an adaptive trigger circuit positioned within the housing and configured to detect an impedance between the return electrode and the treatment electrode as the treatment electrode moves along a face of the user and to trigger the current output circuit to apply the microcurrent based on the impedance.

According to an embodiment, a method for applying a therapeutic microcurrent includes using a handheld device, measuring an electrical impedance between a treatment electrode of the handheld device in contact with a person's face and a return electrode at the surface of the handheld device in contact with the person's hand to produce a detected impedance, converting the detected impedance to a detected impedance variable, and comparing the detected impedance variable to a dynamically determined treatment threshold. An application of a therapeutic microcurrent through the treatment electrode and the present location on the person's face is triggered if the detected impedance variable satisfies the treatment threshold. The therapeutic microcurrent is not triggered if the detected impedance variable does not satisfy the treatment threshold. The treatment threshold is updated using the detected impedance variable.

According to an embodiment, a handheld sinus treatment device includes a current output circuit for applying microcurrent to a triggered location on a human user and an adaptive trigger circuit configured to detect impedance values at locations on a person's face, dynamically establish a triggering threshold, and trigger the current output circuit for applying microcurrent when the dynamically established triggering condition is met.

According to an embodiment, a method includes measuring an electrical impedance between a treatment electrode of a sinus treatment device and a return electrode of the sinus treatment device on a face of a user as the treatment electrode moves across the face of the user and the return electrode is in contact with a hand of the user. The method includes generating an impedance variable based on the electrical impedance, comparing the impedance variable to a treatment threshold, and passing a therapeutic microcurrent between the treatment electrode and the return electrode through the face of the user responsive to the detected impedance variable satisfying the treatment threshold.

BRIEF DESCRIPTION OF THE DRAWINGS

FIG. 8 illustrates an example flow chart illustrating an example process of operating a sinus treatment device, according to an embodiment of the disclosure.

FIG. 9 illustrates an example flow chart illustrating an example process of operating a sinus treatment device, according to an embodiment of the disclosure.

DETAILED DESCRIPTION

Figure 1:
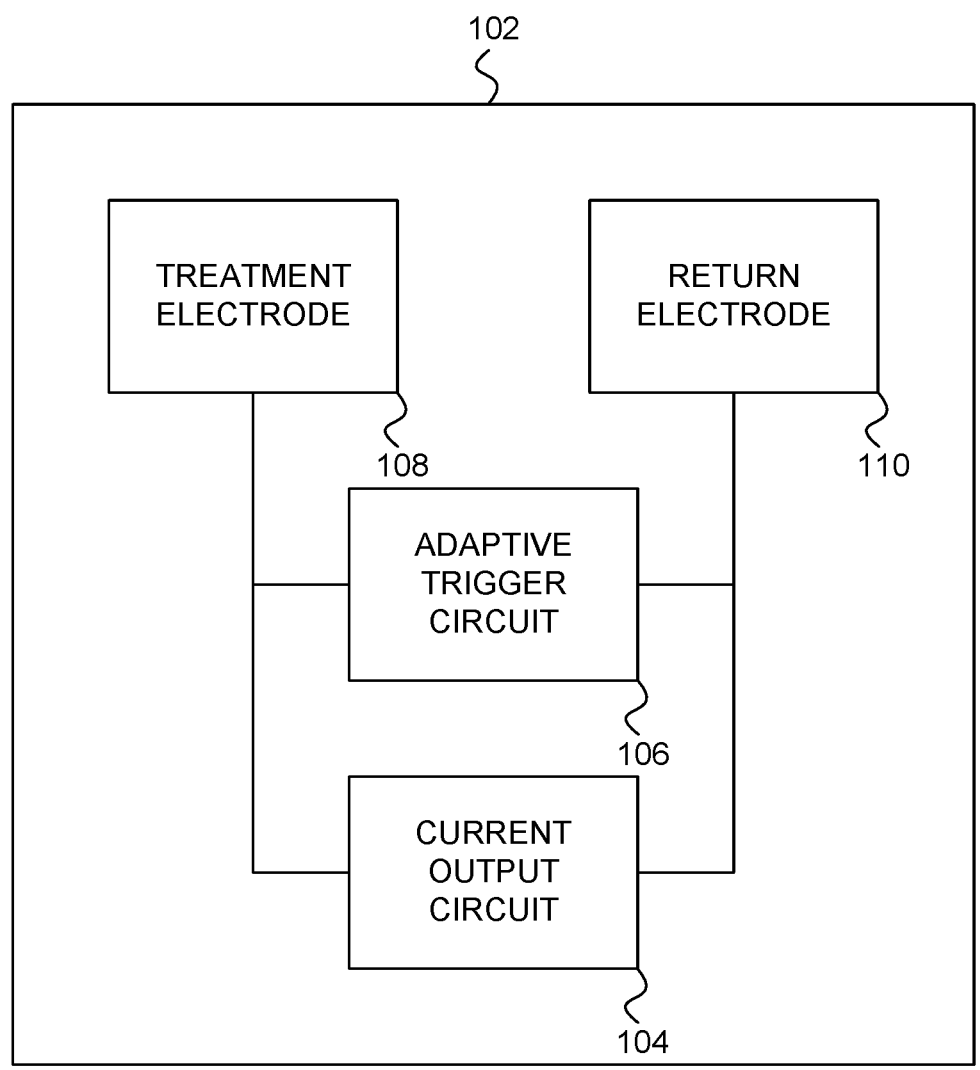
FIG. 1 is a block diagram of a sinus treatment device, according to an embodiment.

In the following detailed description, reference is made to the accompanying drawings, which form a part hereof. In the drawings, similar symbols typically identify similar components, unless context dictates otherwise. Other embodiments may be used and/or other changes may be made without departing from the spirit or scope of the disclosure.

FIG. 1 is a block diagram of a handheld sinus treatment device 102, according to an embodiment.

According to an embodiment, the handheld sinus treatment device 102 is configured to provide sinus relief treatment to the user by providing electrical sinus treatment stimulation to treatment locations adjacent to the sinuses of the user. In a detection mode, the handheld sinus treatment device 102 detects a treatment location by outputting a detection signal to a treatment electrode 108 of the handheld sinus treatment device 102 as the user glides the treatment electrode of the handheld sinus treatment device 102 over the skin adjacent to the sinuses of the user. Electrical current is returned through the body of the user via a return electrode 110. An adaptive trigger circuit 106 receives a sequence of detection signals and derives a dynamic threshold for triggering a treatment mode.

The handheld sinus treatment device 102 identifies the treatment location based on the detection signal in comparison to the dynamic threshold. When the handheld sinus treatment device 102 has identified a treatment location, the handheld sinus treatment device 102 enters into a treatment mode. In the treatment mode, the handheld sinus treatment device 102 outputs therapeutic current from a current output circuit 104 through the treatment electrode 108. The therapeutic current is selected to provide sinus relief treatment stimulation to the treatment location, thereby providing sinus relief to the user. The user can operate the handheld sinus treatment device 102 to identify and provide treatment to multiple treatment locations.

Figure 2A:
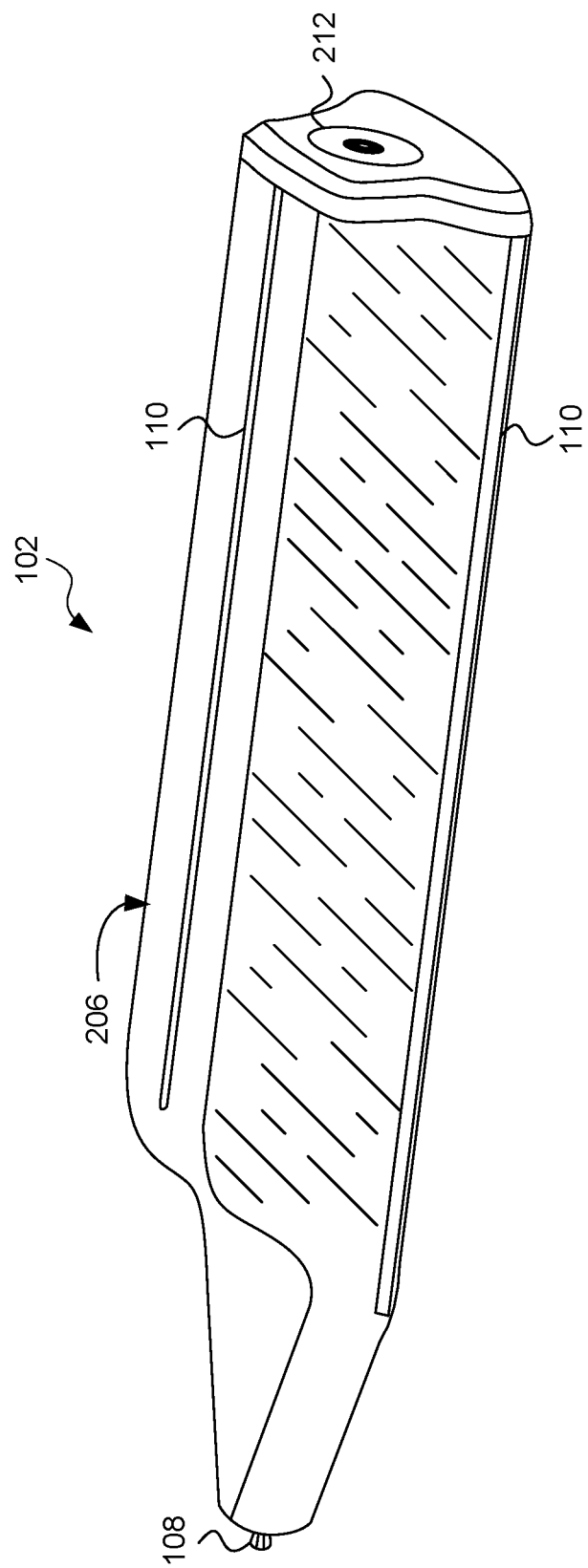
FIG. 2A is a perspective view of a handheld sinus treatment device, according to an embodiment.

FIG. 2A is a perspective view of a handheld sinus treatment device 102, according to an embodiment. The handheld sinus treatment device 102 includes a body or housing 206, a treatment electrode 108, a return electrode 110, and a charging port 212, according to an embodiment.

According to an embodiment, the body 206 is a rigid casing or housing. The body 206 has a shape that enables a user of the handheld sinus treatment device 102 to securely grip and comfortably hold the handheld sinus treatment device 102 during operation of the handheld sinus treatment device 102. The body 206 can be made from a material that is not electrically conductive. The body 206 can be made from a material that has low thermal conductivity. The body 206 is configured to protect sensitive electronic circuitry positioned within the body 206, as is described in more detail with relation to FIG. 3.

According to an embodiment, the treatment electrode 108 is an electrical conductor placed at a tip of the body 206. The treatment electrode 108 can include a rounded shape at a point of contact with the skin of the user such that the treatment electrode 108 can be placed against the skin of the user comfortably without piercing or scratching the skin. Furthermore, the shape and material of the treatment electrode 108 can be selected to enable the user to comfortably glide the treatment electrode 108 along the skin of the user's face adjacent to sinuses of the user.

According to an embodiment, the return electrode 110 includes an electrically conductive material positioned at various locations on or in the body 206. The return electrode 110 can be positioned in the body 206 at positions selected so that when the user holds the handheld sinus treatment device 102 in the user's hand, the user's hand is in contact with the return electrode 110 on one or more locations on the body 206. According to an embodiment, the return electrode 110 can include a conductive polycarbonate or other conductive polymer. In another embodiment, the return electrode 110 can include a conductive metal such as stainless steel, copper, nickel plated copper, chromium plated copper, gold, silver, aluminum, or plated aluminum, for example.

According to an embodiment, the charging port 212 is positioned at the rear of the body 206 of the handheld sinus treatment device 102. The charging port 212 is configured to receive a charging cable. When the charging cable is connected to the charging port 212, the internal battery of the handheld sinus treatment device 102 is recharged. Additionally, or alternatively, the charging port 212 can be a power supply port configured to connect to a power cable that provides power to the handheld sinus treatment device 102 while the user is using the handheld sinus treatment device 102. The charging port 212 can be a micro USB port, a USB 2.0 port, a USB 3.0 port, a USB C port, or any other kind of port that can be utilized to charge the battery of the handheld sinus treatment device 102, or to otherwise provide power to the handheld sinus treatment device 102. Additionally, or alternatively, the handheld sinus treatment device 102 can include wireless charging capability. For example, the handheld sinus treatment device 102 can include circuitry that enables inductive charging of the battery of the handheld sinus treatment device 102 such that when the handheld sinus treatment device 102 is positioned on a charging dock, the battery is recharged by inductive charging.

Figure 2B:
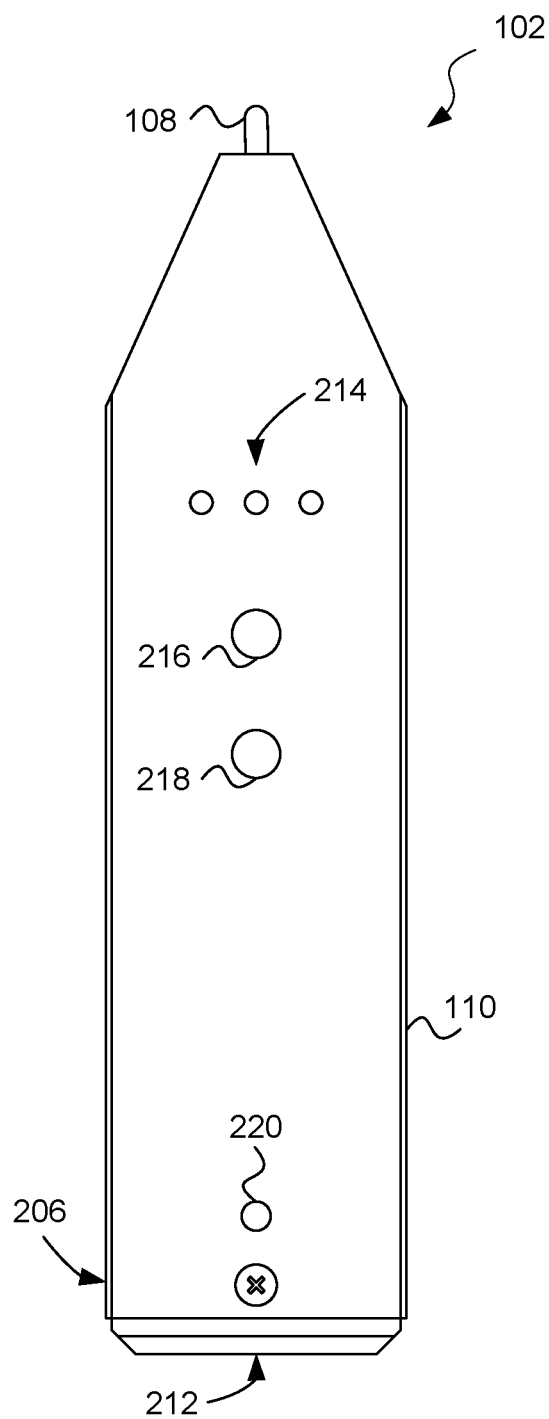
FIG. 2B is a top view of the handheld sinus treatment device of FIG. 2A, according to an embodiment.

FIG. 2B is a top view of a handheld sinus treatment device 102, according to an embodiment. The top view of the handheld sinus treatment device 102 illustrates the body 206, the treatment electrode 108, the return electrode 110, indicators 214, a sensitivity setting button 216, a power button 218, and a low battery indicator 220.

According to an embodiment, the indicators 214 can provide an indication of the sensitivity level of the handheld sinus treatment device 102. The sensitivity level corresponds to a sensitivity setting for detecting treatment areas adjacent to the sinuses of the user. For example, the indicators 214 can provide an indication of a relative level of a dynamically established condition for triggering. The indicators 214 can include multiple LED indicators. The handheld sinus treatment device 102 can illuminate a number of the sensitivity level indicator LEDs 214 to indicate a sensitivity level of the handheld sinus treatment device 102 during a detecting mode. A greater number of illuminated indicator LEDs 214 can correspond to a higher sensitivity level. A lesser number of illuminated indicator LEDs 214 can correspond to a lower sensitivity level. Alternatively, other schemes for illuminating LEDs to indicate a sensitivity level of the detecting mode of the handheld sinus treatment device 102 can be utilized. Additionally, the indicators 214 can include indicators other than LEDs. For example, the indicators 214 can include various types of lights, a display panel, or other types of indicators capable of providing an indication of the sensitivity level of the handheld sinus treatment device 102 during a detecting mode of the handheld sinus treatment device 102. According to an embodiment, the indicators 214 can also signal that a treatment location has been identified, that treatment stimulation is currently being provided, that another treatment location should be identified, or other parameters of operation of the handheld sinus treatment device 102.

According to an embodiment, the sensitivity setting button 216 is configured to enable the user to manually adjust the sensitivity (condition for triggering) of the handheld sinus treatment device 102 during a detecting mode. The user can manipulate the sensitivity setting button 216 in order to increase or decrease the sensitivity of the handheld sinus treatment device 102. For example, the user can press the sensitivity setting button 216 to adjust the sensitivity of the handheld sinus treatment device 102. Additionally, or alternatively, the user can toggle or slide the sensitivity setting button 216 in order to adjust the sensitivity of the handheld sinus treatment device 102. Additionally, or alternatively, the sensitivity setting button 216 can include multiple buttons for adjusting the sensitivity of the handheld sinus treatment device 102. A first button can be used to decrease the sensitivity. A second button can be used to increase the sensitivity. Additionally, or alternatively, the handheld sinus treatment device 102 can include a touchscreen that enables the user to adjust the sensitivity of the handheld sinus treatment device 102.

According to an embodiment, the power button 218 is configured to enable the user to turn the handheld sinus treatment device 102 on or off. For example, if the handheld sinus treatment device 102 is currently off, then the user can turn the handheld sinus treatment device 102 on by pressing, toggling, sliding, or otherwise manipulating, the power button 218. If the handheld sinus treatment device 102 is currently on, then the user can turn the handheld sinus treatment device 102 off by pressing, toggling, sliding, or otherwise manipulating the power button 218. Alternatively, the sensitivity setting button 216 and the power button 218 can be implemented in a single button or switch that can adjust the sensitivity or turn the handheld sinus treatment device 102 on or off based on a length of a button press, a number of button presses, or other types of manipulations of the single button.

According to an embodiment, the low battery indicator 220 can provide an indication of a state of charge of the battery of the handheld sinus treatment device 102. The low battery indicator 220 can include one or more LEDs. When the battery of the handheld sinus treatment device 102 is low, one or more LEDs of the low battery indicator 220 can become illuminated. If the low battery indicator 220 includes a single LED, then the single LED can become illuminated when the battery is nearing depletion. Conversely, the single LED may not be illuminated when the battery is not nearing depletion. Alternatively, when the battery is nearing depletion, a first LED of a first color can be illuminated to indicate that the battery is nearing depletion. If the battery is not nearing depletion, then a second LED of a second color can be illuminated indicating that the battery is not nearing depletion.

According to an embodiment, portions of the return electrode 110 are positioned on the sides of the body 206 of the handheld sinus treatment device 102. When the user grips the handheld sinus treatment device 102 such that a thumb of the user is in a position to manipulate the sensitivity setting button 216 and the power button 218, the palm and/or fingers of the hand of the user will be in contact with the portion of the return electrode 110 positioned on the sides of the body 206 of the handheld sinus treatment device 102.

Figure 2C:
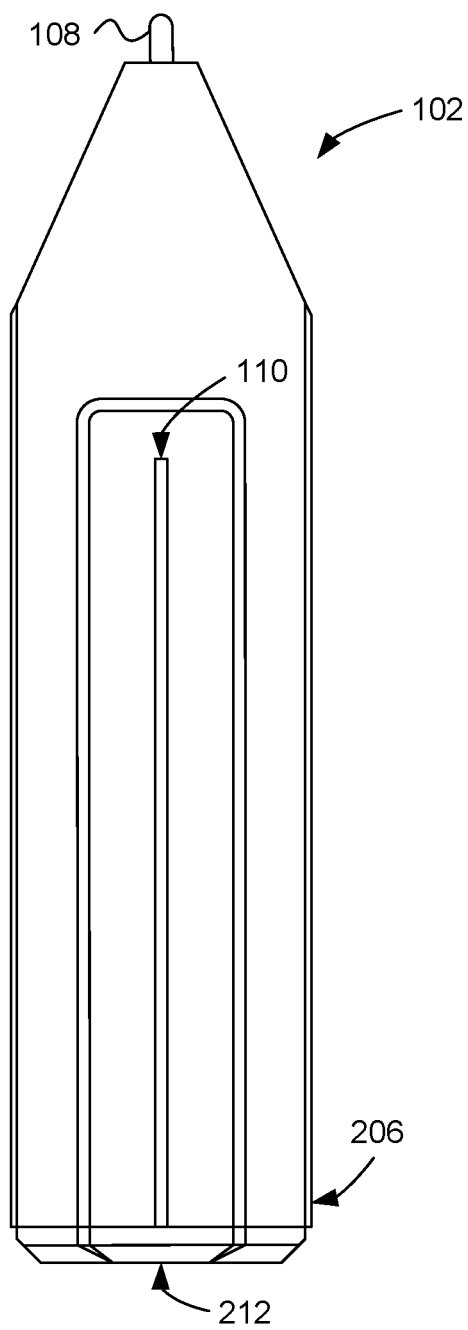
FIG. 2C is a bottom view of the handheld sinus treatment device of FIG. 2A, according to an embodiment.

FIG. 2C is a bottom view of the handheld sinus treatment device 102 of FIG. 2B, according to an embodiment. The bottom view of the handheld sinus treatment device 102 illustrates a portion of the return electrode 110 positioned on the bottom portion of the body 206 of the handheld sinus treatment device 102. The positioning of a portion of the return electrode 110 on the bottom of the body 206 of the handheld sinus treatment device 102 further ensures that when the user holds the handheld sinus treatment device 102 in the user's hand, the user's hand will be in contact with the return electrode 110.

Figure 3:
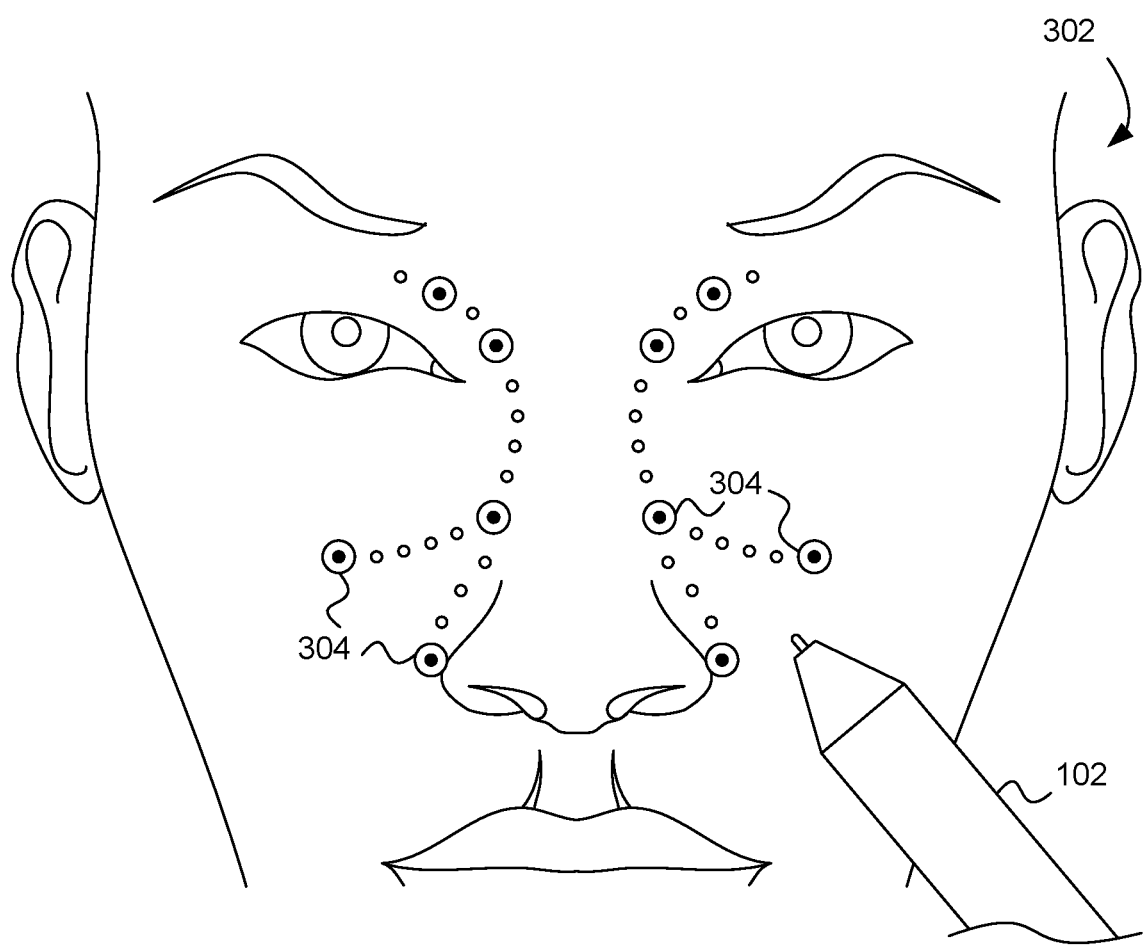
FIG. 3 is an illustration highlighting a plurality of sinus treatment areas adjacent to the sinuses of a user, according to an embodiment.

FIG. 3 is an illustration of a face 302 of a user of the handheld sinus treatment device 102 highlighting treatment areas 304. According to an embodiment, the treatment areas 304 correspond to nerve nodes. The nerve nodes are locations at which sinus nerves pass through the skull. The treatment areas 304 are characterized by reduced electrical impedance compared to locations between the nerve nodes.

According to an embodiment, a user uses the handheld sinus treatment device 102 by holding the body 206 in one hand such that the user's hand is in contact with portions of the return electrode 110. The user then places the treatment electrode 108 on the skin adjacent to the sinuses and glides the treatment electrode 108 over the skin during a detection mode of the handheld sinus treatment device 102. In the detection mode, the handheld sinus treatment device 102 detects variations in electrical impedance as the user glides the treatment electrode 108 over the skin.

Figure 4:
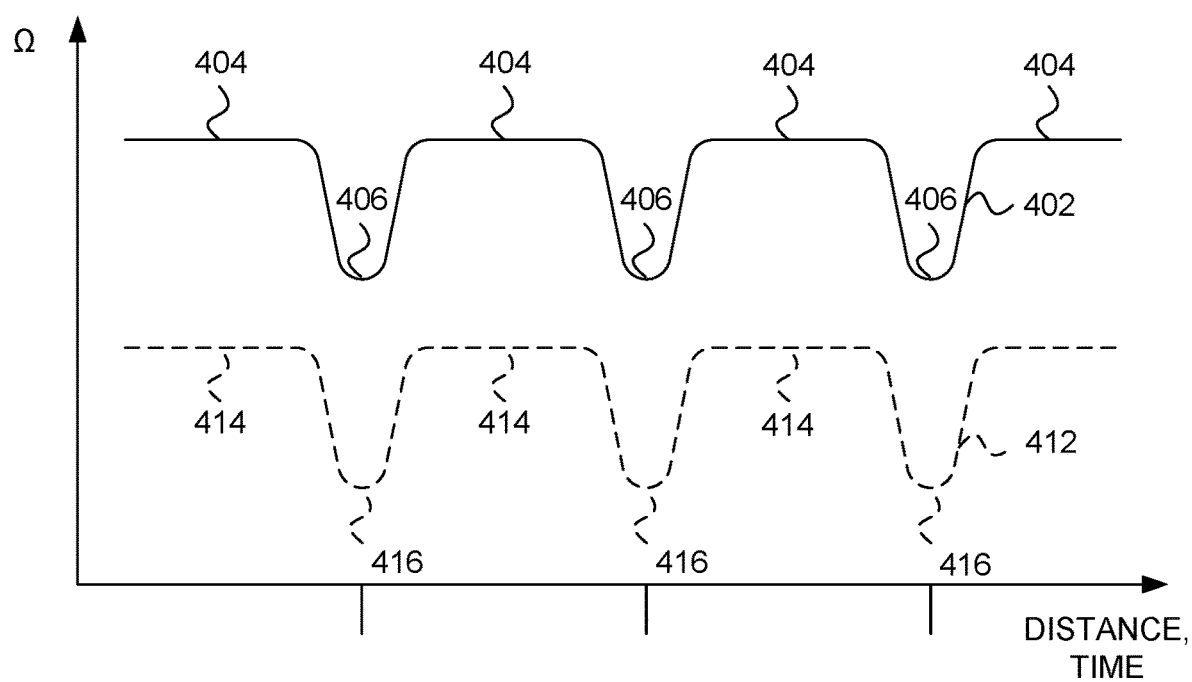
FIG. 4 is a diagram showing impedance variations that may be detected as a treatment electrode is glided over a path across the skin that intersects several nerve nodes shown in FIG. 3, according to an embodiment.

FIG. 4 is a diagram showing impedance variations that may be detected as the treatment electrode 108 is glided over a path across the skin that intersects several treatment areas 304 shown in FIG. 3, according to an embodiment. An impedance curve 402 shows ohms ($\Omega$) corresponding to a sequence of locations across the face of the user. Low impedance regions 406 corresponding to treatment areas 304 shown in FIG. 3. Higher impedance regions 404 separate the low impedance regions 406 corresponding to desired treatment areas 304. A second curve 412 represents an impedance curve measured at a different time. In the second curve 412, higher impedance regions 414 separate the low impedance regions 416 corresponding to desired treatment areas 304. The second curve 412 may correspond to a second user, for example. However, the second curve 412 can represent measured impedance across a corresponding skin path at a different time. Relative humidity, hydration, skin oil, and various physiological variations can cause an impedance curve 402 to shift to a second curve 412 at a different time or on a different day. Accordingly, there is a need to accommodate the change in impedance to avoid triggering between nodes and/or to trigger at all at another instance.

According to an embodiment, one approach for changing triggering impedance is to provide a sensitivity setting button 216 (FIG. 2B) for manually selecting a "sensitivity" for the triggering circuit. Other approaches described herein allow for dynamically determining a triggering condition using an adaptive trigger circuit 106 (FIG. 1).

According to an embodiment, electrical impedance between the treatment electrode 108 of the handheld sinus treatment device 102 in contact with a sequence of points 304 on a person's face and a current return electrode 110 is detected to produce a sequence of detected impedance values. The detected impedance is converted to a detected impedance variable. For example, in one embodiment converting the detected impedance to a detected impedance variable consists essentially of performing an analog-to-digital conversion to create a digital detected impedance variable. The detected impedance variable is compared to a dynamically determined treatment threshold. If the detected impedance variable satisfies the treatment threshold, the current output circuit 104 is triggered to cause an application of a therapeutic microcurrent through the treatment electrode 108. If the detected impedance variable does not satisfy the treatment threshold, the device continues in detection mode and an application of the therapeutic microcurrent is not triggered. The treatment threshold is updated using the most recently detected impedance variable. In some embodiments, the treatment threshold is only updated if the detected impedance variable does not satisfy the treatment threshold. In other embodiments, the treatment threshold is updated whether or not the most recently detected impedance variable satisfies the treatment threshold.

The inventors contemplate several approaches to performing adaptive triggering.

According to an embodiment, the dynamically determined impedance threshold comprises a dynamically determined impedance value and satisfaction of the impedance threshold occurs when the detected impedance variable has a value equal to or less than the dynamically determined impedance value.

According to an embodiment, an averaging circuit creates the dynamic threshold as 80% of an average digital impedance value for the higher impedance regions 404. If the detected impedance variable has a value less than 80% of the average digital impedance value for three successive measurements, then the dynamic threshold is satisfied and a therapeutic current is applied. If the detected impedance variable has a value greater than 80% of the average digital impedance value, then the dynamic threshold is not satisfied and the most recent detected impedance variable is averaged into the average for the high impedance regions 404. Other thresholds may be substituted for 80% of the high impedance average and different numbers of successive measurements may be applied. For example, in one embodiment, the noise filter (the number of successive measurements) may be decreased if the detected impedance variable has a lower value. In another embodiment, a higher threshold of 90% of the high impedance average may be used.

In another embodiment, detected impedance variables are distributed into a bimodal distribution. High impedance measurements are averaged into a non-treatment area average. Low impedance measurements are averaged into a treatment area average. A dynamic threshold equal to halfway between the non-treatment area average and the treatment area average may be set, wherein the therapeutic microcurrent is applied if the most recent three detected impedance variable values falls below the treatment threshold. Other thresholds may be substituted for halfway between the non-treatment area average and the treatment area average. For example, treatment may be applied closer to the center of the treatment areas 304 by selecting an impedance variable threshold lower than halfway between the non-treatment area and the treatment area averages. Optionally, a user-controlled sensitivity setting may select from amongst a range of thresholds between the two ranges.

According to an embodiment, a slope between a number of adjacent measurement points is determined, with the treatment threshold corresponding to an average slope in detected impedance between a number of most recent measurements. Higher slopes correspond to larger excursions in impedance, which correspond to lower values of impedance at the low impedance regions 406. In an embodiment, slope vs. distance may be estimated as a difference in successive measurements. Three to five successive slopes that exceed an average slope between successive measurements in a higher impedance region 404 by at least 20% may constitute a treatment threshold.

In an embodiment converting the detected impedance to a detected impedance variable can include determining a first derivative of the detected impedance. In an embodiment, converting the detected impedance to a detected impedance variable can include determining a slope of the detected impedance relative to recently detected impedance instances.

According to an embodiment, converting the detected impedance to a detected impedance variable includes determining (in combination with previous detected impedances) a second derivative of the detected impedance. In effect, this corresponds to using the detected impedance to determine a curvature of the detected impedance relative to recently detected impedance instances.

According to an embodiment, as impedance decreases from a higher impedance region 404 entering a low impedance region 406, curvature (second derivative) successively increases as the impedance decreases, then curvature decreases as the curve passes through an inflection point, then curvature increases again as impedance approaches a minimum. An inflection point may operate as an estimate of an edge between a non-treatment area 404 and a treatment area 406. In practice, second derivative in a digital processor, may be approximated as a difference between successive differences in digital impedance value. Since both the upper edges and the bottoms of the treatment areas 406 have high curvature, a region of zero curvature between a region of high negative curvature and a region of high positive curvature, over an appropriate number of samples, represents an edge of a treatment area 406.

According to an embodiment, two or more detected impedance variables may be compared to a corresponding two or more thresholds to determine a global threshold for the detection of a treatment area 406. For example, crossing an edge between a non-treatment area 404 and a treatment area 406 may be estimated by requiring a relatively high slope (first derivative) AND requiring a change in sign of a curvature (second derivative).

According to an embodiment, temporal proximity to a most recent treatment may be used in combination with one or more thresholds to determine a triggering state. As may be appreciated from inspection of FIG. 3, the treatments areas 304 are dispersed across the face 302. In practice, impedance measurements are taken at frequent intervals compared to the ability of a person to glide the treatment electrode across his or her face 302. Accordingly, if a new threshold is satisfied too quickly, for example less than 250 milliseconds or 500 milliseconds, after the most recent completed treatment, it may be inferred that the new threshold satisfaction does not represent encountering a new treatment area 304, and triggering may be suppressed.

According to an embodiment, it is desirable, for effective treatment, to apply a therapeutic microcurrent to a point sufficiently close to a nerve node (treatment area 304) for a majority of the current to pass along the nerve fiber. This situation may be satisfied if the treatment electrode is within 200 to 500 millimeters of the center of a node (treatment area 304). Accordingly, the determination of a treatment threshold being satisfied can be considered generally close enough if the treatment electrode is within such a conduction distance of the nerve node, according to one embodiment.

According to an embodiment, in the treatment mode, the handheld sinus treatment device 102 provides treatment stimulation to the treatment area 304, corresponding to the nerve that is located during the detection mode. The handheld sinus treatment device 102 can provide treatment stimulation to the treatment area 304 by providing electrical stimulation to the treatment area 304. The electrical stimulation can affect the nerve node at the treatment area 304 in such a way that the user experiences relief from troubling sinus symptoms such as pain, congestion, inflammation, or other unpleasant symptoms.

According to an embodiment, the handheld sinus treatment device 102 is a transcutaneous electrical nerve stimulation (TENS) device. The handheld sinus treatment device 102 applies electrical treatment stimulation in the form of a microcurrent having selected characteristics. The microcurrent can have an average magnitude that is multiple orders of magnitude lower than common TENS devices. According to an embodiment, the microcurrent does not have a DC component, but is characterized by current spikes of alternating polarity. According to an embodiment, the treatment stimulation is provided at each treatment area 304 for a period of time between 2-10 seconds.

According to an embodiment, the treatment electrode 108 is the active electrode of a monopolar design. The housing/body 206 of the handheld sinus treatment device 102 may serve as the return electrode 110 when return electrodes 110 are integrated into the body 206. A user's hand holding the handheld sinus treatment device 102 completes the electrical path from the conductive treatment electrode 108 to the return electrode(s) 110 in that microcurrents may travel from conductive treatment electrode 108, through the nasal area of a user and down to the hand of the user that is contacting the return electrode(s) 110, in an embodiment. These microcurrents may be referred to as "stimulation currents" in this disclosure.

According to an embodiment, in the detection mode, the user presses the conductive treatment electrode 108 to the skin and the handheld sinus treatment device 102 initiates a low-frequency circuit that is maintained at a constant current. The handheld sinus treatment device 102 may use the current to calculate the impedance in the path between the tissue at the treatment electrode 108 and the hand in contact with the handheld sinus treatment device 102. The handheld sinus treatment device 102 remains in the detection mode until the detection current indicates that a treatment threshold has been met. The position of the treatment electrode 108 when the impedance meets the treatment threshold corresponds to a treatment area 304. The treatment area 304 corresponds to a nerve node area. When the handheld sinus treatment device 102 identifies a treatment area 304 based on a comparison of a detected impedance variable to a dynamically determined treatment threshold, the handheld sinus treatment device 102 can enter the treatment mode and can deliver treatment stimulation to the identified treatment area 304.

According to an embodiment, the handheld sinus treatment device 102 can indicate to the user that the handheld sinus treatment device 102 is in the treatment mode and that the user should hold the treatment electrode 108 at the treatment area 304 for a selected period of time. According to an embodiment, the handheld sinus treatment device 102 can indicate the transition between the detection mode and the treatment mode by the indicators 214. The indicators 214 can include one or more LEDs that can provide an illumination scheme that indicates whether the handheld sinus treatment device 102 is in the detection mode or the treatment mode. According to an embodiment, the handheld sinus treatment device 102 can indicate that the handheld sinus treatment device 102 is in the treatment mode via haptic feedback (vibration). According to an embodiment, the handheld sinus treatment device 102 can indicate whether the handheld sinus treatment device 102 is in the detection mode, the treatment mode, or transitioning between the detection and treatment nodes by a combination of haptic feedback and LED indicators 214. According to an embodiment, when the handheld sinus treatment device 102 enters the treatment mode as indicated by one or more of LED indicators 214 and haptic feedback, the user holds the handheld sinus treatment device 102 in place until the treatment period has passed as indicated by cessation of haptic and LED indicators 214 (approximately 8 seconds in one example).

According to an embodiment, once the treatment period ends, the handheld sinus treatment device 102 resets to detection mode. The user then may continue to glide the handheld sinus treatment device 102 along the indicated path until reaching the next treatment area 304 as identified based on a new comparison a detected impedance variable to the dynamically determined treatment threshold. The user may adjust the impedance sensitivity of the handheld sinus treatment device 102, in one embodiment. Changes in sensitivity adjust the impedance threshold at which the handheld sinus treatment device 102 will enter treatment mode. Changes in sensitivity do not change the output current, in one embodiment. In another embodiment, changes in the dynamically determined treatment threshold correspond to differences in impedance, and the change in sensitivity can be used to correct for a different impedance in order to maintain approximately constant current during treatment.

According to an embodiment of a treatment circuit of the disclosed handheld sinus treatment device 102, the constant current stimulation output is approximately 1 Hz-1000 Hz, bi-phasic, no DC component signal with an average current of approximately 1000 µA over a resistive load of 10K-100K Ω. The signal is presented to the patient by means of the treatment electrode 108, in one embodiment. According to an embodiment, the spring-loaded tip activates the circuit and gently ramps the current to provide maximal comfort to user.

According to an embodiment, constant current stimulation circuit output is directed to the active treatment electrode 108 (the device tip) and returned to the circuit by way of the return electrode 110 (metallized portions of the enclosure). When the circuit is completed by the user pressing the device tip 108 to the face, a microcontroller monitors the resulting stimulation current and controls the stimulation voltage (across the treatment electrode 108 and return electrode 110) to maintain the desired current, in one embodiment. The impedance of the circuit is then calculated and monitored by the microcontroller. In the event that the impedance falls below a specified threshold, which is indicative of a treatment area 304, the microcontroller presents a treatment prompt through the user interface (UI), in one embodiment. According to an embodiment, the user is instructed to maintain the device tip 108 location until the treatment prompt has timed out. After treatment time out, the user is instructed to slowly move the device tip 108 to the next detected treatment area 304, in one embodiment.

According to an embodiment, the sensitivity level setting determines the impedance threshold at which the handheld sinus treatment device 102 will signal the user to detection of a treatment area 304. The treatment sensitivity threshold may be increased to compensate for higher impedance associated with dry skin or the presence of makeup, in one embodiment. Upon detection of a treatment area 304, the haptic motor starts to vibrate and the sensitivity level indicator LEDs 214 flash for a pre-programmed period of time, in one embodiment. If the calculated impedance increases above the threshold (device tip 108 removed from the face 302 or moved to a higher impedance location on the face 302), the treatment session may be terminated.

Figure 5:
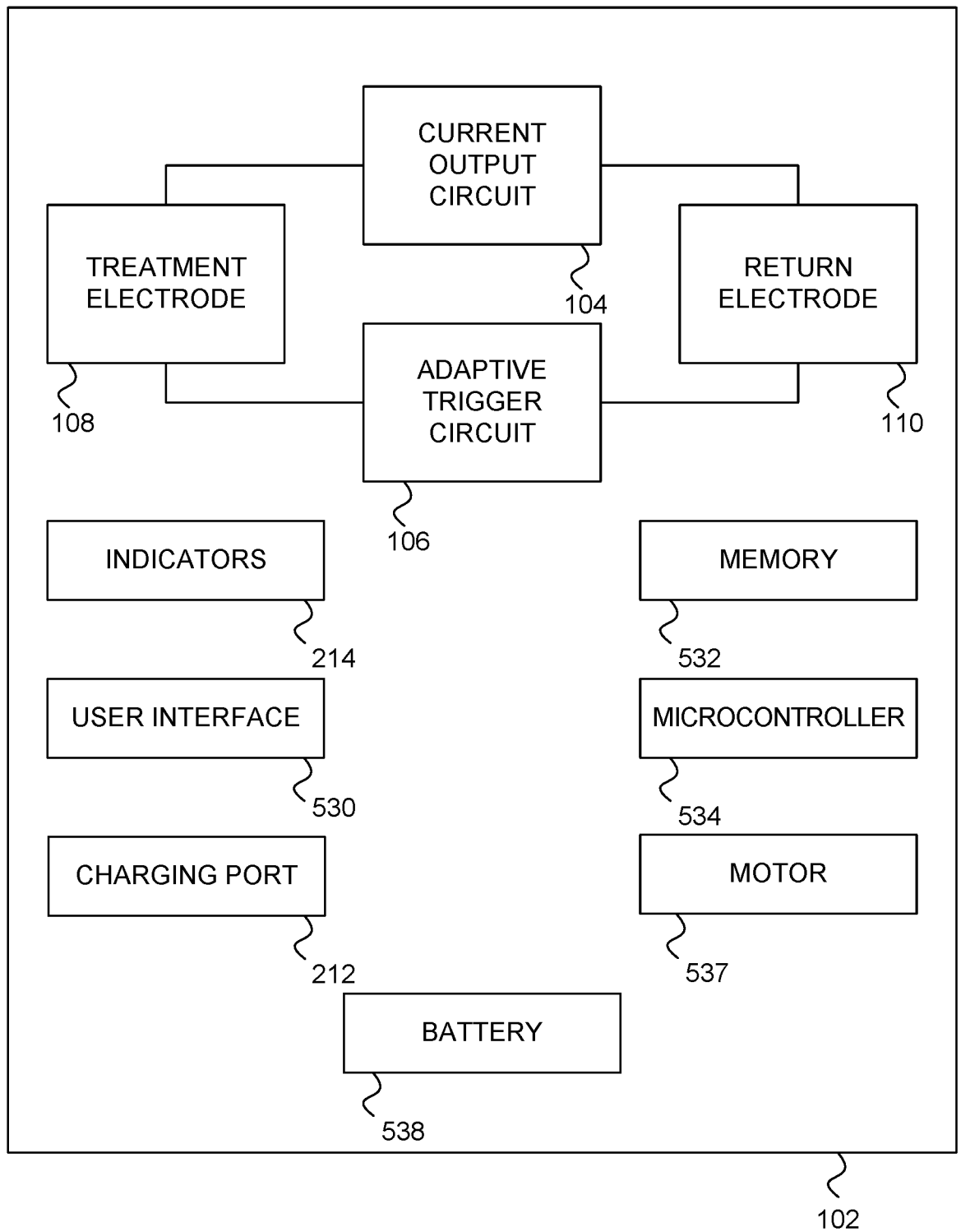
FIG. 5 is a block diagram of a handheld sinus treatment device, according to an embodiment.

FIG. 5 is a block diagram of the handheld sinus treatment device 102, according to an embodiment. The handheld sinus treatment device 102 includes a treatment electrode 108, a return electrode 110, a current output circuit 104, an adaptive trigger circuit 106, the charging port 212, indicators 214, a user interface 530, a memory 532, a microcontroller 534, a motor 537, and a battery 538. The current output circuit 104 is shown as separate from the treatment electrode 108 and the return electrode 110 for purposes of clarity. Similarly, the current output circuit 104 is shown as separate from the adaptive trigger circuit 106 for purposes of clarity. In practice both circuits may use a common current source, but with a voltage divider or resistance being placed between selectable nodes of the circuit. The handheld sinus treatment device 102 utilizes these components to provide effective sinus relief treatments to the user.

According to an embodiment, the treatment electrode 108 and the return electrode 110 cooperate together to provide both detection currents and treatment stimulation. Detection and treatment currents are passed between the treatment electrode 108 and the return electrode 110 through the body of the user. In particular, the treatment electrode 108 is positioned in contact with the user's skin to the sinus areas of the user. The return electrode 110 is in contact with the user's hand as the user holds the handheld sinus treatment device 102. The detection and treatment currents pass between the treatment electrode 108 and return electrode 110 via the hand, body, and facial skin of the user.

According to an embodiment, the indicators 214 provide indications to the user as to the current mode of operation of the handheld sinus treatment device 102. Indicators 214 can include one or more LEDs that can be illuminated in selected ways to indicate whether the handheld sinus treatment device 102 is powered on, whether the handheld sinus treatment device 102 is in a treatment mode, whether the handheld sinus treatment device 102 is in a detection mode, whether the handheld sinus treatment device 102 awaits user input, or indications of other types of functionality of the handheld sinus treatment device 102. According to an embodiment, the indicators 214 can include a display capable of outputting text or images to indicate to the user the various functions of the handheld sinus treatment device 102.

According to an embodiment, the user interface 530 includes various components that enable the user to control functionality of the handheld sinus treatment device 102. The user interface 530 can include the on-off power button 218, the sensitivity setting button 216, or other kinds of buttons, switches, touchscreens, or input controls that enable the user to control functionality of the handheld sinus treatment device 102. The user can manipulate the user interface 530 in order to control the functionality of the handheld sinus treatment device 102.

According to an embodiment, the memory 532 stores data related to the functionality of the handheld sinus treatment device 102. The memory 532 can include software instructions by which the various functionalities of the handheld sinus treatment device 102 can be implemented. The memory 532 can include reference impedance values and/or threshold impedance values. The reference and threshold impedance values can be utilized in the detection mode of the handheld sinus treatment device 102. The memory 532 can include data indicating previously detected treatment areas 304. The memory 532 can include other settings such as treatment lengths, treatment stimulation strengths, frequencies of treatments, or other settings including default settings and user selected settings for operation of the handheld sinus treatment device 102. The memory 532 can include one or more of EEPROMs, flash memory, ROMs, SRAM, DRAM, or other kinds of computer readable media capable of storing instructions that can be executed by the microcontroller 534.

According to an embodiment, the motor 537 enables the handheld sinus treatment device 102 to provide haptic feedback to the user. For example, during a treatment mode in which the handheld sinus treatment device 102 provides stimulation treatment to a treatment area 304, the motor 537 can cause the handheld sinus treatment device 102 to vibrate mildly to indicate to the user that the handheld sinus treatment device 102 is in the treatment mode. The motor 537 can cease the vibration to indicate that the handheld sinus treatment device 102 is no longer in the treatment mode. The motor 537 can generate vibrations to provide a variety of types of indications to the user of the handheld sinus treatment device 102.

According to an embodiment, the battery 538 provides power to the handheld sinus treatment device 102. The battery 538 can include a rechargeable battery that enables the user to recharge the battery 538 after the battery 538 has become depleted through use. The battery 538 can be a lithium-ion battery, a NiCad battery, a carbon zinc battery, an alkaline battery, a nickel metal hydride battery, or other types of batteries.

According to an embodiment, the charging port 212 enables the user to recharge the battery 538. For example, the charging port 212 can be configured to receive a charging cable that connects the charging port 212 to a power source. Charging port 212 can include a micro USB port, a USB 2.0 port, a USB 3.0 port, a USB C port, or other types of charging ports. According to an embodiment, the charging port 212 enables the charging and data transmission. When a charging cable is plugged into the charging port 212, the battery 538 can be charged and data can be received or transmitted over the charging cable via the charging port 212. According to an embodiment, the handheld sinus treatment device 102 can operate while a charging cable is attached to the charging port 212. Thus, if the battery 538 is depleted, the user can attach a charging cable to the charging port 212 and can operate the handheld sinus treatment device 102 from power received via the charging port 212.

According to an embodiment, the microcontroller 534 controls the functionality of the other components of the handheld sinus treatment device 102. The microcontroller 534 is communicatively coupled to the treatment electrode 108, the return electrode 110, the indicators 214, the memory 532, the user interface 530, the wireless transceiver 536, and the charging port 212.

According to an embodiment, the microcontroller 534 executes the software instructions stored in the memory 532 to implement the various modes of functionalities of the handheld sinus treatment device 102. The microcontroller 534 causes the treatment electrode 108 and the counter electrode 110 to pass the detection currents in the detection mode, and to pass the treatment microcurrents in the treatment mode. The microcontroller 534 controls the indicators 214 to indicate the various modes of functionalities of the handheld sinus treatment device 102. The microcontroller 534 communicates with the user interface 530 to enable the user to select various modes of operation of the handheld sinus treatment device 102. The microcontroller 534 controls the functionality of the wireless transceiver 536.

According to an embodiment, when wireless signals are received by the wireless transceiver 536 from the personal electronic device 104, the microcontroller 534 receives and processes the wireless signals. The microcontroller 534 can execute instructions contained in the wireless signals. The microcontroller 534 can write to the memory 532 control data received in the wireless signals. The microcontroller 534 can read data from the memory 532 in accordance with instructions received in the wireless signals.

Figure 6:
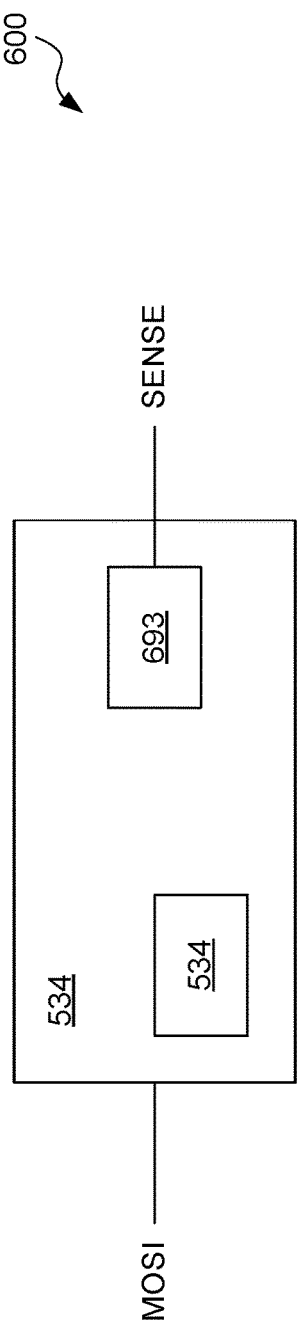
FIG. 6 illustrates an example of sinus treatment circuitry for use with a sinus treatment device, according to an embodiment of the disclosure.
Figure 6:
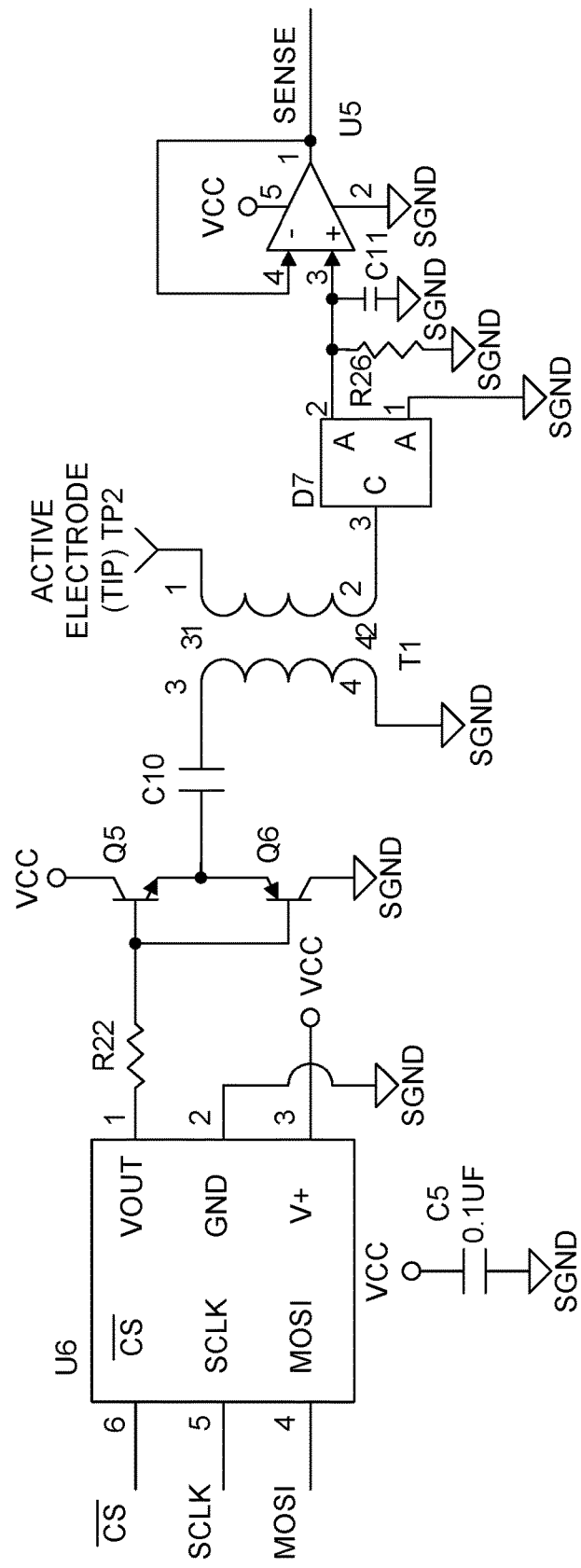

FIG. 6 illustrates an example sinus treatment circuitry 600 for use with the handheld sinus treatment device 102, according to an embodiment of the disclosure. The sinus treatment circuitry 600 is positioned within the housing/body 106, according to one embodiment. The sinus treatment circuitry 500 includes a microcontroller 534 including a memory 532 and an analog-to-digital converter (ADC) 693. In the illustrated embodiment of FIG. 5, the sinus treatment circuitry 500 also includes a stimulation driver stage and a peak detector.

According to an embodiment, the stimulation driver stage is coupled to apply a stimulation voltage between the treatment electrode (active electrode TP2) and the return electrode 110 (not illustrated in FIG. 5). In the illustrated embodiment, the stimulation driver stage includes a digital-to-analog converter (DAC), an amplifier, a transformer, and a capacitor. According to an embodiment, the DAC (U6) is coupled to generate an analog voltage (pin 1 of U6, VOUT) in response to a digital instruction from the microcontroller 534 received via the MOSI (Master Out Slave In) communication channel of pin 4 of U6.

In the illustrated embodiment, the amplifier includes transistors Q5 and Q6 and is coupled to generate an amplified analog voltage (emitter node of Q5) in response to receiving the analog voltage from the DAC (U6).

In the illustrated embodiment, the transformer T1 includes a primary side (nodes 3 and 4) and a secondary side (nodes 1 and 2). The treatment electrode (active electrode TP2) is coupled to node 1 of the secondary side of the transformer T1, in the illustrated embodiment.

In the illustrated embodiment, capacitor C10 is coupled between the amplifier and a primary side of the transformer T1 to block the DC (direct current) portions of the amplified analog signal.

According to an embodiment, the peak detector includes a diode element, a buffer circuit, and a sample and hold circuit. In the illustrated embodiment, the diode element is D7. According to an embodiment, the buffer circuit is coupled to output a peak stimulation current signal. According to an embodiment, the peak detector is coupled to generate a peak stimulation current signal on the node 1 output of op-amp U5 in response to receiving a stimulation signal from the treatment electrode. In the illustrated embodiment, the stimulation signal may travel from the treatment electrode TP2 to node 2 of the transformer T1 via node 1 of the transformer T1.

According to an embodiment, the sample and hold circuit is coupled between the diode element (e.g., D7) and the buffer circuit and the diode element is coupled between the secondary side of the transformer and the sample and hold circuit. In the illustrated embodiment, the sample and hold circuit includes resistors R26 and capacitor C11.

According to an embodiment, the microcontroller 534 is coupled to receive the peak stimulation current signal (SENSE) from the peak detector and coupled to the stimulation driver stage for adjusting the stimulation voltage in response to the peak stimulation current signal. According to an embodiment, the microcontroller 534 dynamically adjusts the stimulation voltage to keep the peak stimulation current signal at a constant value. According to an embodiment, microcontroller 534 includes ADC 693 coupled to sample the peak stimulation current signal and drive the digital instruction to the DAC (via MOSI communication channel) to keep the peak stimulation current signal at the constant value.

The sinus treatment circuitry 600 of FIG. 6 provides a means to maintain a nearly constant (and comfortable) stimulation current in response to varying resistance or impedance. Turning to a more specific description of an embodiment of sinus treatment circuitry 600, a digital-to-analog converter (DAC) U6 receives commands from the microcontroller 534 to generate a square wave with a variable amplitude of 0 to +Vcc volts. The DAC output is current limited by R22 and is used to drive a push-pull output power stage comprised of Q5 and Q6, in the illustrated embodiment. The output of the push-pull stage is AC coupled by C10 and drives the primary side of a step-up transformer T1. C10 blocks the DC component of the square wave and allows through only the rising and falling edges of the square wave. The transformer converts the high current, low voltage edge input to the high voltage, low (microcurrent) stimulation current output, in the illustrated embodiment.

One end of the secondary side of the transformer is connected to the treatment electrode. The other end of the secondary coil is connected to a dual diode array D7. The diode array acts as the stimulation current positive peak detector. R26 and C11 provide a simple sample and hold function of the detected peak. The peak detector output is buffered by op-amp U5. The output of the op-amp is then sampled by the ADC of the microcontroller.

During use, a control loop is formed by the DAC, peak detector, and the microcontroller ADC. The sensed positive peaks of the stimulation current are maintained at a constant level by controlling the DAC output. As the total resistance decreases, the control loop reduces the DAC output which reduces the amplitude of the edges being input to the transformer. The control loop effectively converts the voltage source output of the transformer to a constant current source, in the illustrated embodiment. In this manner, any uncomfortable surges in current are reduced during treatment.

Figure 7:
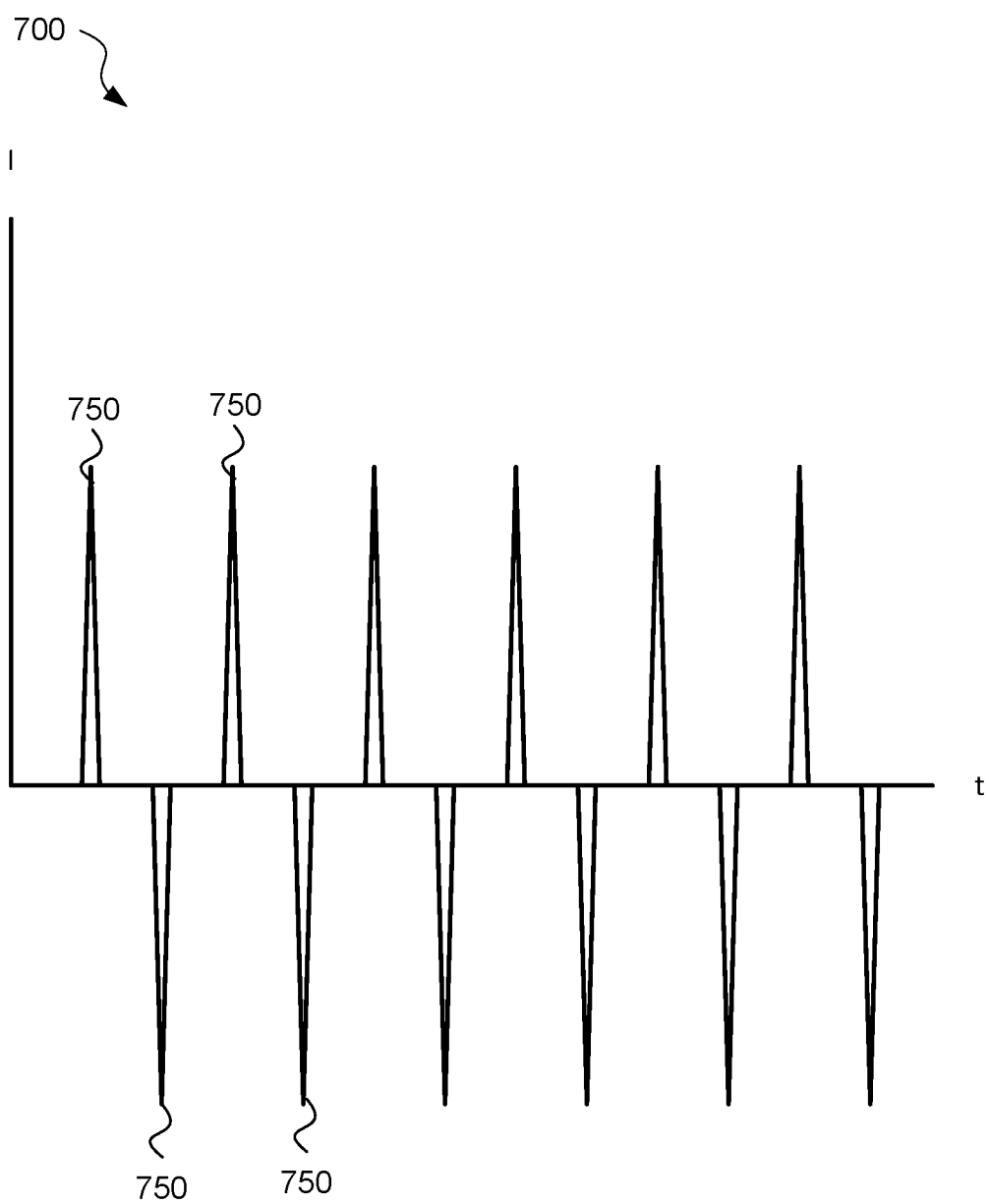
FIG. 7 is a graph of a treatment current vs time, according to an embodiment of the disclosure.

FIG. 7 is a graph of a treatment microcurrent (I) vs time (t), according to an embodiment. The treatment microcurrent is applied during a treatment mode of the handheld sinus treatment device 102 after the handheld sinus treatment device 102 has identified a treatment location. The treatment microcurrent provides relief to sinus discomfort and users.

According to an embodiment, the treatment microcurrent corresponds to a series of sharp current spikes 750 or peaks. According to an embodiment, successive current spikes 750 alternate in direction such that every other current spike flows in a first direction, while intervening current spikes flow in a second, opposite, direction. According to an embodiment, the current spikes 750 correspond to the rising and falling edges of a square wave voltage signal. According to an embodiment, the treatment microcurrent is generated by feeding a square wave voltage signal to a transformer, such as the transformer T1, via a capacitor, such as the capacitor C10. Those of skill in the art will recognize, in light of the present disclosure, that a treatment microcurrent in accordance with FIG. 7 can be generated in various ways. All such other ways for generating the treatment microcurrent fall within the scope of the present disclosure.

According to an embodiment, the treatment microcurrent has no DC offset. The lack of a DC offset can enhance the therapeutic effect of the treatment microcurrent. This is because, in one interpretation, the rapid changes in current magnitude and direction promote physiological effects that do not occur in the presence of a DC current.

According to an embodiment, the sinus treatment circuitry 600, including the microcontroller 534 and the memory 532, adjust the stimulation voltage between the treatment electrode and the return electrode to maintain a constant treatment microcurrent during the treatment mode. According to an embodiment, maintaining a constant treatment microcurrent corresponds to causing the peaks of the treatment microcurrent to have substantially the same magnitudes. According to an embodiment, maintaining a constant treatment microcurrent corresponds to causing the peaks of the treatment microcurrent to have substantially the same absolute values. Thus, the positive current peaks and the negative current peaks have the same absolute value, in one embodiment. Alternatively, maintaining a constant treatment microcurrent corresponds to causing the positive current peaks to have a same first magnitude, and causing the negative current peaks to have a same second magnitude.

According to an embodiment, the peaks of the sinus treatment microcurrent have a magnitude less than or equal to 1000 μA. According to an embodiment, the peaks of the treatment microcurrent have a magnitude less than or equal to 600 μA. According to an embodiment, the sinus treatment microcurrent spikes 750 have an average current less than or equal to 1000 μA. According to an embodiment, the sinus treatment microcurrent spikes have an average current less than or equal to 600 μA.

According to an embodiment, the frequency of the treatment microcurrent is less than 1000 Hz. According to an embodiment, the period of a single treatment microcurrent cycle corresponds to the time between current peaks of the same direction. According to an embodiment, the frequency of the treatment microcurrent is between 1 Hz and 100 Hz. According to an embodiment, the spikes in the treatment microcurrent make up less than 10% of a single cycle. According to an embodiment, the spikes in the treatment microcurrent make up less than 5% of a single cycle. According to an embodiment, the spikes in the treatment microcurrent make up about 3% of a single cycle.

According to an embodiment, during the treatment mode, the handheld sinus treatment device 102 measures the impedance by measuring the peaks of the treatment microcurrent. According to an embodiment, the handheld sinus treatment device 102 adjusts a stimulation voltage applied between the treatment electrode 108 and the return electrode 110 to bring the magnitude of the peaks of the treatment microcurrent back to a desired constant value.

According to an embodiment, in the detection mode in which the handheld sinus treatment device identifies treatment locations, the handheld sinus treatment device 102 measures the impedance by applying a detection current with a waveform similar or identical to the treatment microcurrent waveform and measuring the magnitude of the current peaks of the detection current in order to determine the impedance. According to an embodiment, the handheld sinus treatment device 102 measures the impedance by passing a detection current with a smaller magnitude than the treatment microcurrent. According to an embodiment, during the detection mode, the handheld sinus treatment device 102 applies a detection voltage that is lower than the stimulation voltage applied during the treatment mode. According to an embodiment, the handheld sinus treatment device measures the impedance by passing a detection current with a waveform entirely different than the treatment microcurrent waveform.

In one embodiment, during the treatment mode, the handheld sinus treatment device 102 measures the impedance by measuring the current spikes 750 or peaks of the treatment current. In one embodiment, the handheld sinus treatment device 102 adjusts a stimulation voltage applied between the conductive tip 108 and the return electrode 110 to bring the magnitude of the current spikes 750 or peaks of the treatment current back to a desired constant value.

Those of skill in the art will recognize, in light of the present disclosure, that in practice the treatment current may vary from the graph 600. For example, the risetime and fall time of a given current spike may not be identical. The rise times and fall times of separate current spikes may not be identical to each other. A given current spike 750 can include, at the tail end, a brief portion that flows in the opposite direction to the primary direction of the current spike 750. In a constant current situation, current spikes may have slightly differing magnitudes while remaining substantially the same. There may be noise present among the current waveform. All such variations from the graph 700 fall within the scope of the present disclosure.

In one embodiment, in the detection mode in which the handheld sinus treatment device identifies treatment locations, the handheld sinus treatment device 102 measures the impedance by applying a detection current with a waveform similar or identical to the treatment current waveform and measuring the magnitude of the current peaks of the detection current in order to determine the impedance. In one embodiment, the handheld sinus treatment device 102 measures the impedance by passing a detection current with a smaller magnitude than the treatment current. In one embodiment, during the detection mode, the handheld sinus treatment device 102 applies a detection voltage that is lower than the stimulation voltage applied during the treatment mode. In one embodiment, the handheld sinus treatment device measures the impedance by passing a detection current with a waveform entirely different than the treatment current waveform.

In one embodiment, the current spikes 750 are sharp increases in current followed by a sharp drop in current. In one embodiment, the rise time and fall time of a current spike 750 makes up 90% or more of the current spike 750.

FIG. 8 is a flowchart of a process 800 for operating a handheld sinus treatment device, according to one embodiment. At 802, an electrical impedance is measured, during a detection node of a sinus treatment device, between a treatment electrode and the sinus treatment device and the return electrode of the sinus treatment device as the treatment electrode moves across a face of the user and the return electrode is in contact at the hand of the user, according to one embodiment.

At 804, a trigger condition is established, during the detection node, based on the impedance, according to one embodiment.

At 806, a treatment mode of the sinus treatment device is triggered when the trigger condition is met, according to one embodiment.

At 808, a therapeutic microcurrent is passed, during the treatment mode, between the treatment electrode and the return electrode through the face of the user, according to one embodiment.

FIG. 9 is a flowchart of a process 900 for operating a handheld sinus treatment device, according to one embodiment. At 902, an electrical impedance is measured between the treatment electrode of the handheld sinus treatment device in contact with a sequence of points on a user's face and the return electrode at the surface of the handheld device in contact with the user's hand to produce a detected impedance, according to one embodiment.

At 904 the detected impedance is converted to a detected impedance variable, according to one embodiment At 906 the detected impedance variable is compared to a dynamically determined treatment threshold, according to one embodiment.

At 908, an application of a therapeutic microcurrent is triggered if the detected impedance variable satisfies the treatment threshold. Application of the therapeutic microcurrent is not triggered if the detected impedance variable does not satisfy the treatment threshold. The therapeutic microcurrent is applied through the treatment electrode and the present location of the user's face, according to one embodiment.

At 910, the treatment threshold is updated using the detected impedance variable, according to one embodiment.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A method, comprising:
   measuring, during a detection mode of a sinus treatment device, an electrical impedance between a treatment electrode of the sinus treatment device and a return electrode of the sinus treatment device as the treatment electrode moves across a face of a user and the return electrode is in contact with a hand of the user;
   converting the electrical impedance to a detected impedance variable by performing an analog to digital conversion;
   establishing, during the detection mode, a trigger condition based on the detected impedance variable;
   triggering a treatment mode of the sinus treatment device when the trigger condition is met; and
   passing, during the treatment mode, a therapeutic microcurrent between the treatment electrode and the return electrode through the face of the user by applying a treatment stimulation voltage between the treatment electrode and the return electrode.

2. The method of claim 1, wherein the therapeutic microcurrent includes a series of current spikes.

3. The method of claim 1, wherein the trigger condition includes an impedance threshold; and
   wherein satisfaction of the impedance threshold includes the detected impedance having a value equal to or less than the impedance threshold.

4. The method of claim 1, wherein the trigger condition is based on a first derivative of the detected impedance.

5. The method of claim 1, further comprising turning off the sinus treatment device when the electrical impedance between the treatment electrode and the return electrode is greater than a pre-determined threshold for a pre-determined time period.

6. A method, comprising:
   measuring, during a detection mode of a sinus treatment device, an electrical impedance between a treatment electrode of the sinus treatment device and a return electrode of the sinus treatment device as the treatment electrode moves across a face of a user and the return electrode is in contact with a hand of the user;
   establishing, during the detection mode, a trigger condition based on the electrical impedance;
   triggering a treatment mode of the sinus treatment device when the trigger condition is met; and
   passing, during the treatment mode, a therapeutic microcurrent between the treatment electrode and the return electrode through the face of the user by applying a treatment stimulation voltage between the treatment electrode and the return electrode, wherein the trigger condition is based on a slope of the detected impedance relative to recently detected impedance instances.

7. A method, comprising:
   measuring, during a detection mode of a sinus treatment device, an electrical impedance between a treatment electrode of the sinus treatment device and a return electrode of the sinus treatment device as the treatment electrode moves across a face of a user and the return electrode is in contact with a hand of the user;
   establishing, during the detection mode, a trigger condition based on the electrical impedance;
   triggering a treatment mode of the sinus treatment device when the trigger condition is met; and
   passing, during the treatment mode, a therapeutic microcurrent between the treatment electrode and the return electrode through the face of the user by applying a treatment stimulation voltage between the treatment electrode and the return electrode, wherein the trigger condition is based on a second derivative of the detected impedance.

8. A method, comprising:
   measuring, during a detection mode of a sinus treatment device, an electrical impedance between a treatment electrode of the sinus treatment device and a return electrode of the sinus treatment device as the treatment electrode moves across a face of a user and the return electrode is in contact with a hand of the user;
   establishing, during the detection mode, a trigger condition based on the electrical impedance;
   triggering a treatment mode of the sinus treatment device when the trigger condition is met; and
   passing, during the treatment mode, a therapeutic microcurrent between the treatment electrode and the return electrode through the face of the user by applying a treatment stimulation voltage between the treatment electrode and the return electrode, wherein the trigger condition is based on a curvature of the detected impedance relative to recently detected impedance instances.

* * * * *